(12) United States Patent
Scheele et al.

(10) Patent No.: US 11,116,711 B2
(45) Date of Patent: Sep. 14, 2021

(54) SOLID COSMETIC HAIR CONDITIONING AGENTS (FOAMS)

(71) Applicant: Henkel AG & Co. KGaA, Duesseldorf (DE)

(72) Inventors: Soeren Scheele, Pinneberg (DE); Manuela Mette, Kleinfeld (DE); Petra Westphal, Neu Wulmstorf (DE); Thomas Schroeder, Hamburg (DE)

(73) Assignee: HENKEL IP & HOLDING GMBH, Duesseldorf (DE)

( * ) Notice: Subject to any disclaimer, the term of this patent is extended or adjusted under 35 U.S.C. 154(b) by 0 days.

(21) Appl. No.: 16/887,243

(22) Filed: May 29, 2020

(65) Prior Publication Data

US 2021/0007956 A1    Jan. 14, 2021

(30) Foreign Application Priority Data

Jul. 10, 2019   (DE) .................... 10 2019 210 153.4

(51) Int. Cl.
| | |
|---|---|
| *A61K 8/41* | (2006.01) |
| *A61K 8/34* | (2006.01) |
| *A61K 8/36* | (2006.01) |
| *A61Q 5/12* | (2006.01) |
| *A61K 8/92* | (2006.01) |
| *A61K 8/02* | (2006.01) |
| *A61K 8/73* | (2006.01) |

(52) U.S. Cl.
CPC ............ *A61K 8/416* (2013.01); *A61K 8/0216* (2013.01); *A61K 8/345* (2013.01); *A61K 8/361* (2013.01); *A61K 8/732* (2013.01); *A61K 8/922* (2013.01); *A61Q 5/12* (2013.01)

(58) Field of Classification Search
CPC ...................................................... A61K 8/416
See application file for complete search history.

(56) References Cited

U.S. PATENT DOCUMENTS

| | | | |
|---|---|---|---|
| 7,282,217 B1 * | 10/2007 | Grimshaw | A61K 9/36 424/479 |
| 2012/0021079 A1 * | 1/2012 | West | A61K 36/38 424/769 |
| 2014/0030202 A1 * | 1/2014 | Simonnet | A61K 8/02 |
| 2020/0093710 A1 * | 3/2020 | Hamersky | A61K 8/02 |
| 2020/0170894 A1 * | 6/2020 | Park | A61K 8/06 |

OTHER PUBLICATIONS

Agrana Starch, Starches for Cosmetics-Product range, Mar. 5, 2019, https://www.agrana.com/fileadmin/inhalte/agrana_group/2017/images/Starch/Folder/Kosmetik/PDB_cosmetic_range_organic_range_2019_en.pdf (Year: 2019).*

* cited by examiner

*Primary Examiner* — Mark V Stevens
*Assistant Examiner* — Alparslan Asan
(74) *Attorney, Agent, or Firm* — Lorenz & Kopf, LLP

(57) ABSTRACT

A solid cosmetic composition contains cationic surfactant, a polyhydric $C_2$-$C_6$ alcohol, $C_8$-$C_{30}$ alcohol or $C_8$-$C_{30}$ carboxylic acid or salt and a starch fraction, a modified starch or a starch derivative and is used for hair care.

7 Claims, No Drawings

SOLID COSMETIC HAIR CONDITIONING AGENTS (FOAMS)

CROSS-REFERENCE TO RELATED APPLICATION

This application claims priority to German Patent Application No. 10 2019 210 153.4, filed Jul. 10, 2019, which is incorporated herein by reference in its entirety.

TECHNICAL FIELD

The application describes solid cosmetic compositions based on surfactants, specific polyols, polysaccharides, fatty alcohols and/or fatty acid(s), in particular solid conditioning compositions which dissolve and foam in contact with water. The application further describes methods for the preparation of solid cosmetic compositions and their use for a conditioning mainly of human hair, but also of the skin of the human body.

BACKGROUND

Surfactant-containing products for a conditioning mainly of human hair, but also of the skin of the human body have been known for a long time and are offered commercially mainly in liquid or paste form in suitable packaging. End consumers take the necessary amount of product from the packaging during use and dispose of it after emptying. Compared to certain conditioners that are sold in solid form, such products offer the user the advantage of easy and quick handling, which is why they dominate the market today. However, this advantage is achieved by accepting certain disadvantages, which will be discussed below. In most cases, the packaging of the described products in liquid or pasty form includes non-recyclable plastic, which is a serious problem from an environmental point of view in view of the constantly growing amount of plastic waste.

A further problem is that previous products usually contained higher quantities of water or water/solvent mixtures, which means that the products have a larger volume and, possibly of greater importance, from a transport point of view, a relatively high weight. This is disadvantageous for several reasons. In times of increasing water scarcity, resources should be saved. Also important from both an environmental and cost perspective is an undesirable, increased transport volume associated with large-volume heavy products. Another interesting point is that worldwide travel activity is constantly increasing. Consumers are therefore increasingly interested in cosmetic products that are easy to transport due to their low weight and volume. This is particularly relevant with regard to air travel, as larger containers containing liquids are generally excluded from being carried in an aircraft cabin, so that a passenger travelling with only hand luggage often finds himself in the situation, due to the cosmetics products dominating the market today, of not being able to take his preferred product selection with him or of having to decant the respective products into smaller containers first, which, however, is generally accompanied by an even higher volume of packaging material.

The provision of alternative product forms with lower water content, contained in more environmentally friendly, e.g. recyclable, packaging in a space-saving manner, is therefore an important objective in the formulation of improved, contemporary and sustainable cosmetic products.

Solid conditioner compositions have been known for some time and fill a market niche. Although they have a very low water or solvent content in general and are often packaged with little material, many people are uncomfortable with their handling, because a started conditioner piece is difficult to transport, often partially dissolves when placed near a shower or bathtub or next to the sink, which is also inefficient, and makes the sink or other storage place look unattractive due to conditioner residues, and because conditioner pieces have a tendency to slip out of the user's hand.

Another disadvantage of known solid conditioner formulations, especially with rather small conditioner pieces, is that it takes some time for enough of the conditioner piece to come off to achieve the desired amount of foam and the desired conditioning effect. On the one hand, this is usually undesirable for users because of the additional time required, and on the other hand, it can be associated with higher water consumption for personal hygiene, as many users do not turn off the water flow of the shower or tap during conditioning. From this point of view, it is therefore not reasonable to market individual application portions of known conditioner formulations, especially in miniaturized form of a known conditioner piece, as their dissolution is too slow, as the formulations of these conditioners are not optimized for marketing in individual application portions.

BRIEF SUMMARY

In view of the problems and requirements described above, the inventors therefore set themselves the task of providing formulations and manufacturing processes suitable for solid cosmetic conditioning agents which, by their nature, are suitable for packaging in individual application portions, as well as methods for the manufacture of the same and uses thereof. In their intensive research efforts, the inventors have established several measures which may contribute to this suitability. Thus, the task of the present disclosure is solved by the formulation of methods and uses described in detail below:

The present disclosure provides:

1. A solid cosmetic composition containing—based on the total weight of the cosmetic composition—
   a) from about 0.1 to about 15.0% by weight of at least one cationic surfactant,
   b) from about 10.0 to about 45.0% by weight of at least one polyhydric $C_2$-$C_6$ alcohol,
   c) from about 1.0 to about 15.0% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid, and
   d) from about 1.0 to about 20.0% by weight of at least one starch fraction, a modified starch and/or a starch derivative.

2. A solid cosmetic composition according to Point 1 containing—based on the total weight of the cosmetic composition—from about 0.1 to about 15% by weight, preferably from about 0.25 to about 10% by weight and particularly preferably from about 0.5 to about 7.5% by weight of cationic surfactant a).

3. A solid cosmetic composition according to one of the Points 1 or 2, containing as cationic surfactant a) at least one compound from the following group of
   i. alkyl quats,
   ii. ester quats,
   iii. quaternary imidazolines,
   iv. amidoamines and/or cationized amidoamines, and
   v. mixtures of these.

4. A solid cosmetic composition according to one of Points 2 or 3, containing one or more cationic surfactants from groups a) i.-v. in amounts from about 0.1 to about 15% by weight, preferably from about 0.25 to about 10% by weight and particularly preferably from about 0.5 to about 7.5% by weight (based on the total weight of the cosmetic composition).
5. A solid cosmetic composition according to one of Points 3 or 4, containing at least one cationic surfactant a) from group i.
6. A solid cosmetic composition according to one of the Points 3 to 5, containing $C_8$-$C_{30}$ alkyl tri $C_1$-$C_4$ alkyl ammonium salts, preferably $C_8$-$C_{24}$ alkyl trimethyl ammonium salts, particularly preferably lauryl trimethylammonium salts, cetyl trimethylammonium salts, stearyl trimethylammonium salts, behenyl trimethyl ammonium salts and/or mixtures thereof, in particular the chloride, methosulfate and/or ethosulfates of these cationic surfactants.
7. A solid cosmetic composition according to one of the Points 3 or 6, containing at least one cationic surfactant a) known under the INCI name "Cetrimonium" and/or "Behentrimonium".
8. A solid cosmetic composition according to one of the Points 3 or 4, containing Cetrimonium chloride.
9. A solid cosmetic composition according to one of the preceding Points, containing the polyhydric $C_2$-$C_6$ alcohol in an amount from about 10.0 to about 45.0% by weight, preferably from about 15.0 to about 40.0% by weight, particularly preferably from about 20.0 to about 35.0% by weight (based on the weight of the composition).
10. A solid cosmetic composition according to any of the preceding Points, containing as polyhydric alcohol b) 1,2-propylene glycol, 1,3-butylene glycol, dipropylene glycol, glycerol and/or diglycerol.
11. A solid cosmetic composition according to one of the Points 9 or 10, containing glycerol.
12. A solid cosmetic composition according to one of the preceding Points, containing component c) in an amount from about 1 to about 15% by weight, preferably from about 2 to about 12% by weight, particularly preferably from about 8 to about 12% by weight (based on the weight of the composition).
13. A solid cosmetic composition according to one of the preceding Points, containing as component c) saturated or unsaturated, branched or unbranched $C_8$-$C_{30}$ carboxylic acids and/or saturated or unsaturated, branched or unbranched $C_8$-$C_{30}$ alcohols, preferably $C_{10}$-$C_{22}$ carboxylic acids and/or $C_{10}$-$C_{22}$ alcohols and in particular coco acids, lauric acid, myristic acid, palmitic acid, stearic acid, behenic acid, oleic acid and mixtures thereof and/or coco alcohols, lauryl alcohol, myristyl alcohol, cetyl alcohol, stearyl alcohol, behenyl alcohol, oleyl alcohol and mixtures thereof.
14. A solid cosmetic composition according to one of Points 12 or 13, containing
    cetyl alcohol,
    stearyl alcohol,
    palmitic acid,
    stearic acid and/or
    mixtures thereof.
15. A solid cosmetic composition according to one of the preceding Points, comprising component d) in an amount from about 1 to about 20% by weight, preferably from about 5 to about 15% by weight and particularly preferably from about 8 to about 12% by weight (based on the total composition).
16. A solid cosmetic composition according to one of the preceding Points, containing as polysaccharide d)
    i. starch fractions from maize, potatoes, rice, wheat and/or tapioca and/or
    ii. modified starches derived from maize, potatoes, rice, wheat and/or tapioca; and/or
    iii. derivatives of starches such as amylose, amylopectin, dextrins.
17. A solid cosmetic composition according to Point 16, containing as polysaccharide d)i. starch fractions from maize.
18. A solid cosmetic composition according to Point 16, containing as polysaccharide d)ii. compounds known under the INCI designation Hydroxypropyl Starch Phosphates.
19. A solid cosmetic composition according to Point 16, containing as polysaccharide d)iii. maltodextrin.
20. A solid cosmetic composition according to Point 16, containing as polysaccharide d) from groups i, ii and iii, preferably starch fractions from maize, compounds known under the INCI designation Hydroxypropyl Starch Phosphates and maltodextrin in the abovementioned amounts.
21. A solid cosmetic composition according to one of the preceding Points, containing—based on the total weight of the cosmetic composition—from about 0.01 to about 10.00% by weight, preferably from about 0.02 to about 8.00% by weight, more preferably from about 0.05 to about 6% by weight, most preferably from about 0.10 to about 5% by weight of at least one oil, fat and/or wax component, preferably a naturally occurring oil, fat or wax.
22. A solid cosmetic composition according to Point 21, containing vegetable oils and/or vegetable butters.
23. A solid cosmetic composition according to one of the Points 21 or 22, containing shea butter (INCI name: *Butyrospermum parkii* (Shea) Butter).
24. A solid cosmetic composition according to one of Points 21 or 22, containing apricot kernel oil, argan oil, jojoba oil, marula oil, almond oil, olive oil, coconut oil and/or sunflower oil.
25. A solid cosmetic composition according to one of the preceding Points, containing water in an amount of up to about 50% by weight, preferably about 47.5% by weight and in particular about 45% by weight (based on the total weight of the composition).
26. A solid cosmetic composition according to one of the preceding Points for the care of human hair, in particular for use after hair cleansing as a leave-on or rinse-off composition.
27. A solid cosmetic composition according to any of the preceding Points 1 to 26 in the form of a porous body which has a density in the range of from about 0.2 g/cm$^3$ to about 1.2 g/cm$^3$ and which converts into an emulsion upon contact with water.
28. A method for preparing a solid cosmetic composition according to Point 27, exemplified by the following steps:
    a. adding all ingredients into a heatable container,
    b. heating the mixture a) until all ingredients are melted and/or uniformly dispersed,
    c. introducing a gas by
        introducing air, $N_2$, $N_2O$ and/or $CO_2$ at a pressure of from about 2 to about 40 bar, or
        introducing air with a high speed mixer, d. extruding the aerated mixture c)
   from a desired shaping port, or
   into a desired mold,
e. solidification/cooling of the extrudate in the desired form,
f. removing the extrudate from the mold or cutting and portioning the extrudate.

29. A solid cosmetic hair care composition, obtainable by the method according to Point 28.
30. A cosmetic method for hair care in which a solid cosmetic composition is moistened, impregnated and/or emulsified with water according to one of the Points 1 to 27, rubbed between the hands and distributed on the hair and after an exposure time of from about 5 seconds to about 5 minutes, optionally rinsed out again with water.
31. A method of using a solid cosmetic composition according to any one of Points 1 to 27, wherein
    a) the solid composition is first mixed with water and then applied to the hair, or
    b) the solid composition is applied directly to the wet hair.
32. The use of a cosmetic composition according to one of Points 1 to 27 for the care of hair.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The first subject-matter of this application is a solid cosmetic composition containing—relative to the total weight of the cosmetic composition—
  a) from about 0.1 to about 15.0% by weight of at least one cationic surfactant,
  b) from about 10.0 to about 45.0% by weight of at least one polyhydric $C_2$-$C_6$ alcohol,
  c) from about 1.0 to about 15.0% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid, and
  d) from about 1.0 to about 20.0% by weight of at least one starch fraction, a modified starch and/or a starch derivative.

The compositions as contemplated herein are solid at about 25° C. Solid compositions within the meaning of the present application are three-dimensional, dimensionally stable structures which are not liquid or gaseous, i.e. which maintain their outer shape even without a surrounding vessel. However, the term "solid" does not imply anything about density or elasticity or other physical properties, so that jellies, brawn, butter etc. may also be solid as contemplated herein as long as they are dimensionally stable at about 25° C.

Such formulation provides the correct properties for single use portions, especially with regard to their dissolution behavior during use. The high concentrations of the active ingredients in such a composition are associated with the advantages that few resources are consumed during production and transport and that the products are easy to transport without great effort or restrictions, even after they have reached the hands of a consumer via the trade, whether to the gym or on a flight.

Cationic surfactants carry a positive charge in their hydrophilic part. This positive charge causes the surfactant molecules to attach themselves to the negatively charged skin and hair surface. In this way, they neutralize the charge, prevent the hair from flying, have a smoothing effect, increase hair shine and improve wet combability. They are primarily used in conditioners, hair rinses and hair treatments, less frequently in shampoos. In addition, cationic surfactants have a co-conserving effect in cosmetic products due to their bactericidal effect.

In principle, all cationic surfactants suitable for use on the human body are suitable as cationic surfactants in compositions as contemplated herein. These are characterized by at least one water-solubilizing, cationic group, such as a quaternary ammonium group, or by at least one water-solubilizing, cationizable group, such as an amine group, and furthermore at least one lipophilic alkyl group with about 6 to 30 C atoms, or also by at least one imidazole group or at least one imidazyl alkyl group.

In general, cationic surfactants are divided into groups according to their structural characteristics. Particularly suitable for use in the compositions as contemplated herein are cationic surfactants a) from at least one of the groups alkyl quats, ester quats, quaternary imidazolines, amidoamines and/or cationized amidoamines.

The present disclosure therefore further concerns a solid cosmetic composition as described above, containing as cationic surfactant a) at least one compound from the following group of
  i. alkyl quats,
  ii. ester quats,
  iii. quaternary imidazolines,
  iv. amidoamines and/or cationized amidoamines, and
  v. mixtures thereof.

These specifically named cationic surfactants a) have shown a conditioning effect in the compositions as contemplated herein which is perceived as particularly pleasant.

Especially preferred compositions as contemplated herein contain as cationic surfactants a)
  quaternary ammonium compounds (alkyl quats) with at least one $C_8$-$C_{24}$ alkyl radical,
  ester quats, and
  amidoamines each having at least one $C_8$-$C_{24}$ acyl radical, and mixtures thereof.

Quaternary ammonium compounds having at least one $C_8$-$C_{24}$ alkyl radical are particularly preferred ammonium halides, in particular chlorides, and ammonium alkyl sulphates, such as methosulfates or ethosulfates, such as $C_8$-$C_{24}$ alkyl trimethylammonium chlorides, $C_8$-$C_{24}$ dialkyl dimethylammonium chlorides and $C_8$-$C_{24}$ methyltrialkylammonium chlorides, for example methylcetyltriammonium chloride, stearyl trimethyl ammonium chloride, distearyl dimethyl ammonium chloride, lauryl dimethyl ammonium chloride, lauryl dimethyl benzyl ammonium chloride and cetyl trimethylammonium chloride, and the imidazolium compounds known under the INCI designations Quaternium-27, Quaternium-83, Quaternium-87 and Quaternium-91. The alkyl chains of the abovementioned surfactants preferably comprise 8 to 24 carbon atoms.

Ester quats are cationic surfactants which contain both at least one ester function and at least one quaternary ammonium group as a structural element and also at least one $C_8$-$C_{24}$ alkyl or $C_8$-$C_{24}$ acyl radical. Preferred ester quats are quaternized ester salts of fatty acids with triethanolamine, quaternized ester salts of fatty acids with diethanol alkylamides and quaternized ester salts of fatty acids with 1,2-dihydroxypropyl dialkylamides. Such products are marketed under the trademarks Stepantex®, Dehyquart® and Armocare®. N,N-bis(2-palmitoyloxyethyl)dimethylammonium chloride, distearoylethyl dimonium methosulfates, distearoylethyl hydroxyethylmonium methosulfates and bis-(isostearoyl/oleoyl isopropyl) dimonium methosulfates are preferred examples of such ester quats.

Bis-(isostearoyl/oleoyl isopropyl) dimonium methosulfate is a particularly preferred ester quat.

Alkyl amido amines are usually produced by amidation of natural or synthetic $C_8$-$C_{24}$ fatty acids and fatty acid sections with di-($C_1$-$C_3$)alkyl amino amines. Compounds from this group of substances which are particularly suitable as contemplated herein are, for example, the compounds known under the INCI designations Stearamidopropyl Dimethylamine, Behenamidopropyl Dimethylamine and/or Bras sic amidopropyl Dimethylamine. Stearamidopropyl Dimethylamine is particularly preferred.

The present disclosure further concerns, in a preferred embodiment, a solid cosmetic composition as described above, containing at least one cationic surfactant a) from group i., preferably $C_8$-$C_{30}$ alkyl tri $C_1$-$C_4$ alkyl ammonium salts and in particular cationic surfactant salts known under the INCI designation "Cetrimonium" and/or "Behentrimonium". Cetrimonium chloride is particularly preferred.

The present disclosure in a further preferred embodiment also concerns a solid cosmetic composition as described above, containing at least one cationic surfactant a) from group ii., preferably quaternized ester salts of fatty acids with diethanol alkylamines and in particular cationic surfactant salts (ester quats ii) known under the INCI designation "Bis-(Isostearoyl/oleoyl Isopropyl) Dimonium".

Compositions preferred as contemplated herein contain at least one cationic surfactant a) in a total amount from about 0.1 to about 15% by weight, preferably from about 0.25 to about 10% by weight, particularly preferably from about 0.5 to about 7.5% by weight, each based on the weight of the composition.

The compositions as contemplated herein may, in addition to conditioning agents, also be cleansing agents. Preferred cleansing agents as contemplated herein may preferably
- be at least one cationic surfactant, preferably in a total amount from about 0.1 to about 2% by weight, more preferably from about 0.2 to about 1% by weight and most preferably from about 0.3 to about 0.5% by weight, each based on the weight of the composition, and
- contain at least one further surfactant selected from anionic, amphoteric, zwitterionic and/or non-ionic surfactants, preferably in a total amount from about 1 to about 40% by weight, more preferably from about 2 to about 35% by weight and particularly preferably from about 3 to about 30% by weight, in each case based on the weight of the composition.

Compositions preferred as contemplated herein further contain at least one polyhydric $C_2$-$C_6$ alcohol b) in a total amount from about 10.0 to about 45.0% by weight, preferably from about 15.0 to about 40.0% by weight, particularly preferably from about 20.0 to about 35.0% by weight, in each case based on the weight of the composition.

The present disclosure further concerns a solid cosmetic composition as described above, containing as polyhydric alcohol b)
- alditols such as mannitol, isomalt, lactitol, sorbitol and xylitol, threat, erythritol and arabitol,
- glycols such as 1,2-propylene glycol, 1,3-butylene glycol, 1,6-hexanediol,
- triols or polyols such as dipropylene glycol, glycerol and/or diglycerol.

Preferred alcohols b) are 1,2-propylene glycol, 1,3-butylene glycol, dipropylene glycol, glycerol and/or diglycerol.

In particular, solid compositions as contemplated herein preferably contain glycerol in the above-mentioned amounts.

These polyhydric alcohols are well tolerated by the skin and as solvents they ensure that the solid cosmetic compositions available with them do not become too solid or too difficult or slow to dissolve.

The present disclosure further concerns a solid cosmetic composition as described above, containing as component c) saturated or unsaturated, branched or unbranched $C_8$-$C_{30}$ carboxylic acids and/or saturated or unsaturated, branched or unbranched $C_8$-$C_{30}$ alcohols, preferably $C_{10}$-$C_{22}$ carboxylic acids and/or $C_{10}$-$C_{22}$ alcohols and in particular coco acids, lauric acid, myristic acid, palmitic acid, stearic acid, behenic acid, oleic acid and mixtures thereof and/or coco alcohols, lauryl alcohol, myristyl alcohol, cetyl alcohol, stearyl alcohol, behenyl alcohol, oleyl alcohol and mixtures thereof.

Solid cosmetic compositions containing cetyl alcohol, stearyl alcohol, palmitic acid, stearic acid and/or mixtures thereof in the proportions or concentrations mentioned are particularly preferred.

These compounds have proved to be particularly suitable structure-giving ingredients for the purposes of the present disclosure. They may be used to formulate cosmetic compositions of sufficient firmness which do not melt too low. They are contained in the compositions as contemplated herein preferably with from about 1 to about 15% by weight, more preferably from about 2 to about 12% by weight, particularly preferably from about 8 to about 12% by weight, in each case based on the weight of the composition.

Polysaccharides d) suitable for present disclosure are composed of more than ten monosaccharide units. Preferred polysaccharides are the starches composed of α-D-glucose units as well as starch degradation products such as amylose, amylopectin and dextrins. As contemplated herein, chemically and/or thermally modified starches are also particularly advantageous, e.g. hydroxypropyl starch phosphate, dihydroxypropyl distarch phosphate or the commercial products Dry Flo®. Dextrans and their derivatives, e.g. dextran sulfate, are also preferred. Also preferred are non-ionic cellulose derivatives, such as methyl cellulose, hydroxypropyl cellulose, hydroxypropyl methyl cellulose or hydroxyethyl cellulose, as well as cationic cellulose derivatives, e.g. the commercial products Celquat® and Polymer JR®, and preferably Celquat® H 100, Celquat® L 200 and Polymer JR® 400 (Polyquaternium-10) as well as Polyquaternium-24. Other preferred examples are polysaccharides from fucose units, e.g. the commercial product Fucogel®.

In the compositions as contemplated herein, the polysaccharides d) are preferably contained in amounts from about 1 to about 20% by weight, preferably from about 5 to about 15% by weight and particularly preferably from about 8 to about 12% by weight, in each case based on the total composition.

The present disclosure further concerns a solid cosmetic composition as described above, containing as polysaccharide d)
i. starch fractions from maize, potatoes, rice, wheat and/or tapioca and/or
ii. modified starches derived from maize, potatoes, rice, wheat and/or tapioca; and/or
iii. derivatives of starches such as amylose, amylopectin, dextrins.

Particularly preferred is a solid cosmetic composition, as described above, containing as polysaccharide d)i. starch fractions from maize.

A solid cosmetic composition, as described above, containing as polysaccharide d)ii. a compound known under the INCI designation Hydroxypropyl Starch Phosphate, is also particularly preferred.

Further particularly preferred is a solid cosmetic composition, as described above, containing as polysaccharide d)iii. maltodextrin.

A solid cosmetic composition, as described above, containing polysaccharides d) from groups i, ii and iii, preferably starch fractions from maize, compounds known under the INCI designation Hydroxypropyl Starch Phosphate and maltodextrin, are particularly preferred.

These polysaccharides have proved to be well suited as stabilizing agents in the context of the present disclosure claimed here. Their application makes it possible to provide ready-made consumer products which retain their properties and appearance in a stable manner over a long period of time and under various environmental conditions.

The present disclosure further concerns a solid cosmetic composition as described above, containing—based on the total weight of the cosmetic composition—from about 0.01 to about 10.00% by weight of at least one oil, fat and/or wax component, preferably a naturally occurring oil, fat or wax.

These are caring substances which help to keep both the skin and hair structure healthy. The defined concentration range allows this care effect to be used but at the same time prevents noticeable greasiness after application of an appropriate composition. Naturally occurring raw materials have the advantage that they regenerate and are therefore sustainable. This aspect is also becoming increasingly important for many users.

The present disclosure further concerns a solid cosmetic composition as previously described, containing vegetable oils and/or vegetable butters.

As already mentioned, naturally occurring raw materials have the advantage that they are renewable and therefore sustainable. This aspect is also becoming increasingly important for many users. Moreover, some vegetable oils or butters, especially if they have been carefully extracted at low temperatures, are extremely potent skin and hair care products as they also contain a multitude of secondary ingredients such as vitamins.

It was discovered that vegetable butters with a melting range of from about 20° C. to about 35° C. are particularly suitable for incorporation into cosmetic compositions as contemplated herein.

Accordingly, vegetable butters with a melting point in the range of from about 20° C. to about 35° C. are particularly preferred as, for example, shea butter (INCI designation: *Butyrospermum parkii* (Shea) Butter), mango butter (INCI designation): *Mangifera Indica* (Mango) Seed Butter), murumuru butter (INCI designation: Astrocaryum Murumuru Seed Butter), cocoa butter (INCI designation: *Theobroma Cacao* (Cocoa) Seed Butter) and/or cupuacu butter (INCI designation: *Theobroma Grandiflorum* Seed Butter).

Cupuacu butter (INCI name: *Theobroma Grandiflorum* Seed Butter) and/or shea butter (INCI name: *Butyrospermum parkii* (Shea) Butter) are particularly preferred and shea butter (INCI name: *Butyrospermum parkii* (Shea) Butter) is particularly preferred.

The at least one vegetable butter (preferably cupuacu butter and/or shea butter, in particular shea butter) is used in the cosmetic compositions as contemplated herein preferably in a proportion by weight of from about 0.01 to about 10.00% by weight, more preferably of from about 0.05 to about 5% by weight, particularly preferably of from about 0.10 to about 1% by weight of the total weight of the compositions.

Oils suitable as contemplated herein are preferably perfume oils and/or vegetable triglyceride oils, such as coconut oil, (sweet) almond oil, walnut oil, peach kernel oil, apricot kernel oil, avocado oil, tea tree oil, soybean oil, cotton seed oil, sesame oil, sunflower oil, tsubaki oil, evening primrose oil, rice bran oil, palm oil, Palm kernel oil, mango kernel oil, cranberry oil, sea buckthorn oil, meadow foam herb oil, thistle oil, macadamia nut oil, grape seed oil, amaranth seed oil, argan oil, bamboo oil, olive oil, wheat germ oil, pumpkin seed oil, mallow oil, hazelnut oil, safflower oil, corn oil, olive oil, rapeseed oil, canola oil, sasanqua oil, jojoba oil, rambutan oil, marula oil and/or quinoa oil.

Especially preferred are apricot kernel oil, argan oil, jojoba oil, marula oil, macadamia nut oil, pumpkin seed oil, amaranth seed oil, quinoa oil, soybean oil, cotton seed oil, sunflower oil, palm oil, palm kernel oil, linseed oil, almond oil, corn oil, olive oil, rapeseed oil, sesame oil, soybean oil, safflower oil, wheat germ oil, peach kernel oil, cranberry oil, sea buckthorn oil and/or coconut oil.

Especially preferred are apricot kernel oil, argan oil, jojoba oil, marula oil, almond oil, olive oil, coconut oil and/or sunflower oil.

The oil(s) may be used in the compositions as contemplated herein preferably in a proportion by weight from about 0.01 to about 10%, more preferably from about 0.05 to about 7%, particularly preferably from about 0.10 to about 5%, of the total weight of the compositions.

In a further preferred embodiment, the present disclosure concerns solid compositions containing water in an amount of up to about 50% by weight, preferably about 47.5% by weight and in particular about 45% by weight (based on their total weight).

In addition to the ingredients described above, the cosmetic compositions as contemplated herein may contain at least one active substance which is advantageously selected from the group comprising plant extracts, humectants, protein hydrolysates, perfumes, UV filters, structurants such as maleic acid, dyes for coloring the composition, active ingredients such as bisabolol and/or allantoin, antioxidants, preservatives such as sodium benzoate or salicylic acid, additional viscosity regulators such as salts (NaCl) or polymers, and pH adjusters such as α and β hydroxycarboxylic acids such as citric acid, lactic acid, malic acid, glycolic acid, and/or bases such as alkanolamines and/or sodium hydroxide.

By suitable plant extracts is meant extracts that may be produced from all parts of a plant. Usually these extracts are produced by extracting the whole plant. However, in some cases it may be preferable to produce extracts exclusively from the flowers and/or leaves of the plant.

Particularly suitable are extracts of *Paeonia lactiflora, Rasa damascena* flower, *Malus domestica* fruit, *Argania spinosa* shell powder, *Laminaria saccharina, Cannabis sativa*, green tea, oak bark, nettle, hamamelis, hops, chamomile, burdock root, horsetail, hawthorn, lime blossom, litchi, almond, aloe vera, spruce needle, horse chestnut, sandalwood, juniper, coconut, mango, apricot, lime, wheat, kiwi, melon, orange, grapefruit, sage, rosemary, birch, mallow, cuckooflower, thyme, yarrow, thyme, lemon balm, cowslip, marshmallow, ginseng, ginger root, *Echinacea purpurea, Olea europea, Boerhavia diffusa* roots, *Foeniculum vulgare* and *Apium graveolens*.

Particularly preferred for use in the compositions as contemplated herein are the extracts from *Paeonia lactiflora, Rosy damascena* flower, *Malus domestica* fruit, *Argania spinosa* shell powder, *Laminaria saccharina, Cannabis sativa*, green tea, nettle, witch hazel, chamomile, aloe vera, ginseng, *Echinacea purpurea, Olea europea* and/or *Boerhavia diffusa* roots.

Water, alcohols and mixtures thereof may be used as extraction agents for the production of the above plant extracts. Among the alcohols, lower alcohols such as ethanol and isopropanol, but in particular polyhydric alcohols such as ethylene glycol and propylene glycol, both as the sole extracting agent and in admixture with water, are preferred. Plant extracts based on water/propylene glycol in a ratio of from about 1:10 to 10:1 have proved to be particularly suitable.

The plant extracts may be used both in pure and diluted form. If they are used in diluted form, they usually contain approx. 2-80% by weight of active substance and the extraction agent or mixture of extraction agents used in their extraction as solvent. The plant extracts may be used in the hair treatment preparations as contemplated herein (based on the total weight of the preparations) preferably in an amount from about 0.01 to about 10% by weight, more preferably from about 0.05 to about 7.5% by weight and in particular from about 0.1 to about 5% by weight.

The present disclosure further concerns a solid cosmetic composition as described above for the care of human hair, in particular for use after hair cleansing as a leave-on or rinse-off composition.

The terms "leave-on" and "rinse-off" mean that the composition is either left in the hair for a relatively short period of time, e.g. possibly for less than one minute or for a few minutes or an hour, until it is rinsed out again, or that the composition remains in the hair until the next hair wash, which may be a few days. Both have certain advantages. A composition that remains on the hair for a long time allows the full care potential of all ingredients to be used, whereas a composition that is to be rinsed out again after a short time may also contain ingredients that have a good care effect but whose longer retention in the hair would be unpleasant.

Preferred in terms of the present disclosure are rinse-off compositions.

The present disclosure further concerns a solid cosmetic composition, as previously described, in the form of a porous body which has a density in the range of from about 0.2 g/cm$^3$ to about 1.2 g/cm$^3$ and which converts into an emulsion in contact with water.

A porous body feels interesting, which enriches the user sensory, and also dissolves well and quickly due to the large surface, which may save time but also water.

The present disclosure further concerns a method of producing a solid cosmetic composition as described above, exemplified by the following steps:
  a) adding all ingredients into a heatable container,
  b) heating the mixture a) until all ingredients are melted and/or evenly dispersed,
  c) introducing a gas by
     introducing air, N$_2$, N$_2$O and/or CO$_2$ at a pressure of from about 2 to about 40 bar, or
     introducing air with a high speed mixer,
  d) extruding the aerated mixture c)
     from a desired shaping port, or
     into a desired mold,
  e) solidification/cooling of the extrudate to the desired shape,
  f) removing the extrudate from the mold or cutting and portioning the extrudate.

Such method has the advantage that it makes the previously described compositions with their respective advantages reproducible and efficiently available.

This method makes ready-made portions of the previously described porous bodies available and their previously described advantages may be experienced.

The present disclosure further concerns a solid cosmetic hair care composition obtainable by the method described above.

The present disclosure further concerns a cosmetic method for hair care in which a solid cosmetic composition as described above is moistened with water, soaked and/or emulsified, rubbed between the hands and distributed on the hair and, after an exposure time of from about 5 seconds to about 5 minutes, rinsed out again with water, if necessary.

The present disclosure further concerns a method of using the solid cosmetic composition as contemplated herein, in which the solid composition is at either first mixed with water and then applied to the hair, or in which the solid composition is applied directly to the wet hair.

This application makes the advantages described above perceptible to a user and thus represents enrichment not only for personal hygiene and care but also a sensory enrichment.

The present disclosure further concerns the use of a cosmetic composition as described above for hair care.

These methods make the advantages described above tangible for a user and thus represent enrichment not only for personal hygiene and care but also a sensory enrichment.

As has been shown by employing the previously described embodiments and their advantages, the process and packaging aspects are important for the present disclosure. They are discussed in more detail below.

In a manufacturing process as contemplated herein, for example, all ingredients are placed in a heatable container, such as, on a laboratory scale, in a suitable vessel in a water bath or on a heating plate, on a production scale rather in a closed and pressurizable vessel, and are mixed and heated, in the case of recipes as contemplated herein, for example at about 75° C. until all ingredients are sufficiently mixed. In such a method, various temperature steps may also be carried out. For example, components may be mixed first which are homogeneously miscible even at a relatively low temperature. This may be done at from about 40° C. to about 50° C. It may also be advantageous to mix in certain ingredients at higher temperatures, for example at from about 85° C. to about 90° C. For this purpose, a method as contemplated herein may comprise one or more steps in this temperature range. Afterwards, one or more steps may be carried out at a lower temperature again, wherein further ingredients are mixed in. Typically, the compositions as contemplated herein solidify at about 65° C., so that certain method steps, such as mixing and extruding the finished mixtures, are not reasonably possible below such a temperature level.

A gas may also be introduced into a mixture resulting from a method described above, including gas mixtures such as air, N$_2$, N$_2$O and/or CO$_2$. This may be done in a boiler, for example at 200-4000 kPa, or by introducing air, for example, using a high-speed mixer or similar equipment. The resulting mixture may then be discharged via an extruder. The mixture expands if it has been under high pressure, as is the case here, and solidifies, for example, at normal room temperature of from about 18° C. to about 25° C., additionally favored by cooling, which goes hand in hand with the expansion of the contained gas. Otherwise, if it was previously mixed under ambient pressure, the mixture only cools down and solidifies by assuming the ambient temperature or by additionally provided cooling.

The introduction of a gas or gas mixture into the compositions as contemplated herein is accompanied by various advantages. As explained at the beginning, a good dissolving behavior is important for solid cosmetic compositions, in particular for compositions which are also intended to be used in single application portions. In addition to the composition, the dissolution behavior may be influenced by the manufacturing and packaging method. For example, by introducing a gas or gas mixture, the surface area where contact with water may take place may be increased, resulting in faster dissolution and the extremely fine bubble structure already established in the solid composition.

Furthermore, it is important to note that cosmetic products have a lot to do with feeling, fun and emotions. Many people relax while taking care of their bodies and enjoy the pleasant feeling of doing something good for themselves. Especially as many people find their everyday life more and more demanding or stressful, small pleasures and playfulness are an important point where stress can be released from a person and satisfaction can be created. Solid cosmetic preparations with an incorporated gas phase, i.e. to a certain extent solid foams, feel different to conventional products, which are perceived as interesting and pleasant.

Foamed solidified emulsions as such have already been mentioned before, but it should be mentioned here that the consistency of the foamed extrudate and the corresponding production equipment allow the realization of imaginative shapes, as known, for example, from meringue.

It is also possible to fill the solid cosmetic compositions as contemplated herein into a jar, for example, made of glass. Since the firmness of these compositions is in a range that allows an application portion to be removed manually, without a tool, from a crucible intended for multiple applications. If the composition has been foamed in a crucible during its manufacture, this gives a particularly interesting sensation.

After a detailed explanation of the various designs and their respective advantages, the presentation of exemplary compositions and an exemplary manufacturing process follows.

Basic exemplary compositions are shown in the following tables 1-4:

TABLE 1

| Ingredient | Z1 | Z2 | Z3 | Z4 | Z5 | Z6 | Z7 | Z8 | Z9 |
| --- | --- | --- | --- | --- | --- | --- | --- | --- | --- |
| a): Cationic surfactant | 0.1-15 | 0.1-14 | 0.15-12.5 | 0.2-11 | 0.25-10 | 0.25-9.5 | 0.3-9.0 | 0.4-8.5 | 0.5-7.5 |
| b): Polyhydric $C_2$-$C_4$ alcohol | 10-45 | 11-44 | 12.5-42.5 | 14-41 | 15-40 | 16-40 | 17.5-40 | 19-40 | 20.0-40 |
| c): Saturated or unsaturated, branched or unbranched $C_8$-$C_{30}$ alcohol; and/or saturated or unsaturated, branched or unbranched $C_8$-$C_{30}$ carboxylic acid and/or a salt of a saturated or unsaturated, branched or unbranched $C_8$-$C_{30}$ carboxylic acid | 1.0-15 | 1.25-14 | 1.5-13.5 | 1.75-13 | 2.0-12 | 3.0-12 | 5.0-12 | 6.0-12 | 8.0-12 |
| d): Polysaccharide | 1.0-20 | 1.25-19 | 1.5-17.5 | 1.75-16 | 5.0-15 | 6.0-14 | 7.0-13.5 | 7.5-13 | 8.0-12 |
| Water and, if necessary, other auxiliary materials and additives | ad 100 | ad 100 | ad 100 | ad 100 | ad 100 | ad 100 | ad 100 | ad 100 | ad 100 |

TABLE 2

| Ingredient | Z11 | Z11 | Z12 | Z13 | Z14 | Z15 | Z16 | Z17 | Z18 |
| --- | --- | --- | --- | --- | --- | --- | --- | --- | --- |
| $C_8$-$C_{24}$ alkyl trimethylammonium salts | 0.1-15 | 0.1-14 | 0.15-12.5 | 0.2-11 | 0.25 10 | 0.25-9.5 | 0.3-9.0 | 0.4-8.5 | 0.5-7.5 |
| 1,2-propylene glycol, 1,3-butylene glycol, dipropylene glycol, glycerol and/or diglycerol | 10-45 | 11-44 | 12.5-42.5 | 14-41 | 15-40 | 16-40 | 17.5-40 | 19-40 | 20-40 |
| Coco acids, lauric acid, myristic acid, palmitic acid, stearic acid, behenic acid, oleic acid, coconut alcohols, lauryl alcohol, myristyl alcohol, cetyl alcohol, stearyl alcohol, behenyl alcohol and/or oleyl alcohol | 1.0-15 | 1.25-14 | 1.5-13.5 | 1.75-13 | 2.0-12 | 3.0-12 | 5.0-12 | 6.0-12 | 8.0-12 |

TABLE 2-continued

| Ingredient | Z11 | Z11 | Z12 | Z13 | Z14 | Z15 | Z16 | Z17 | Z18 |
|---|---|---|---|---|---|---|---|---|---|
| Starch fractions from maize, potatoes, rice, wheat and/or tapioca and/or modified starches derived from maize, potatoes, rice, wheat and/or tapioca and/or derivatives of starches such as amylose, amylopectin, dextrins | 1.0-20 | 1.25-19 | 1.5-17.5 | 1.75-16 | 5.0-15 | 6.0-14 | 7.0-13.5 | 7.5-13 | 8.0-12 |
| Water and, if necessary, other auxiliary materials and additives | ad 100 | ad 100 | ad 100 | ad 100 | ad 100 | ad 100 | ad 100 | ad 100 | ad 100 |

TABLE 3

| Ingredient | Z19 | Z20 | Z21 | Z22 | Z23 | Z24 | Z25 | Z26 | Z27 |
|---|---|---|---|---|---|---|---|---|---|
| Cetrimonium chloride and/or Behentrimonium chloride | 0.1-15 | 0.1-14 | 0.15-12.5 | 0.2-11 | 0.25-10 | 0.25-9.5 | 0.3-9.0 | 0.4-8.5 | 0.5-7.5 |
| Glycerol | 10-45 | 11-44 | 12.5-42.5 | 14-41 | 15-40 | 16-40 | 17.5-40 | 19-40 | 20-40 |
| Palmitic acid, stearic acid, cetyl alcohol and/or stearyl alcohol | 1.0-15 | 1.25-14 | 1.5-13.5 | 1.75-13 | 2.0-12 | 3.0-12 | 5.0-12 | 6.0-12 | 8.0-12 |
| Starch fractions from maize and/or hydroxypropyl starch phosphates and/or maltodextrin | 1.0-20 | 1.25-19 | 1.5-17.5 | 1.75-16 | 5.0-15 | 6.0-14 | 7.0-13.5 | 7.5-13 | 8.0-12 |
| Water and, if necessary, other auxiliary materials and additives | ad 100 | ad 100 | ad 100 | ad 100 | ad 100 | ad 100 | ad 100 | ad 100 | ad 100 |

TABLE 4

| Ingredient | Z28 | Z29 | Z30 | Z31 | Z32 | Z33 | Z34 | Z35 | Z36 |
|---|---|---|---|---|---|---|---|---|---|
| a): Cationic surfactant | 0.1-15 | 0.1-15 | 0.1-15 | 0.1-15 | 0.25-10 | 0.25-10 | 0.25-10 | 0.25-10 | 0.5-7.5 |
| b): Polyhydric $C_2$-$C_4$ alcohol | 10-45 | 10-45 | 10-45 | 10-45 | 15-40 | 15-40 | 15-40 | 15-40 | 20.0-40 |
| c): Saturated or unsaturated, branched or unbranched $C_8$-$C_{30}$ alcohol; and/or saturated or unsaturated, branched or unbranched $C_8$-$C_{30}$ carboxylic acid and/or a salt of a saturated or unsaturated, branched or unbranched $C_8$-$C_{30}$ carboxylic acid | 1.0-15 | 1.0-15 | 1.0-15 | 1.0-15 | 2.0-12 | 2.0-12 | 2.0-12 | 2.0-12 | 8.0-12 |
| d): Polysaccharide | 1.0-20 | 1.0-20 | 1.0-20 | 1.0-20 | 5.0-15 | 5.0-15 | 5.0-15 | 5.0-15 | 8.0-12 |
| f): Oil, fat and/or wax component | 0.01-10 | | | | 0.1-7 | | | | 0.5-5 |
| Plant butter | | 0.01-10 | | 0.01-10 | | 0.1-7 | | 0.1-7 | |
| Triglyceride oil | | | 0.01-10 | 0.01-10 | | | 0.1-7 | 0.1-7 | |
| Water and, if necessary, other auxiliary materials and additives | ad 100 | ad 100 | ad 100 | ad 100 | ad 100 | ad 100 | ad 100 | ad 100 | ad 100 |

Detailed exemplary compositions are shown in the following Table 5:

TABLE 5

| Group | Ingredients | active ingredients contained therein | Z37 | Z38 | Z39 |
|---|---|---|---|---|---|
| 1 | Water | Water | 18 | 36.5 | 36.5 |
| 1 | Citric acid monohydrate | Citric acid | 0.25 | 0.25 | 0.25 |
| 1 | Dehyquart A CA ® | Cetrimonium chloride | 8 | 8 | 8 |
| 1 | Glycerole 99.5% | Glycerol | 35 | 35 | 35 |
| 1 | Cetearyl alcohol | Cetearyl alcohol | 5 | 2 | 2 |
| 1 | Cutina FS 45 ® | Palmitic acid, stearic acid | 5 | 2 | 2 |
| 1 | Cutina GMS-V ® | Glyceryl stearate | 5 | 2.5 | 2.5 |
| 2 | Agenamalt ® 20.225 Maltodextrin DE15 | Maltodextrin | 1 | 1 | 1 |
| 3a | Structure XL ® (28-030A) | Hydroxypropyl starch phosphate | 1.5 | 1.5 | 1.5 |
| 3b | Maisita 9040 ® | *Zea mays* (corn) starch | 17.25 | 10 | 10 |
| 4 | Cetiol SB 45 ® | *Butyrospermum Parkii* (shea) butter | 0.5 | 0.5 | 0.5 |
| 4 | Apricot kernel oil, cold pressed | *Prunus Armeniaca* (apricots) kernel oil | 2 | 2 | 2 |
| 4 | Perfume Tea Grandiosa 611084 | Perfume (fragrance) | 0.5 | 0.5 | 0.5 |
| 4 | Phenoxyethanol, pure | Phenoxyethanol | 1 | 1 | 1 |

The exemplary method for the production of compositions Z37 to Z39 was carried out as follows:

The ingredients were used in the ratio shown in the table above.

Dehyquart A CA was heated in a drum to 40° C. to 50° C. and, in case of an uneven distribution of its ingredients, mixed. After mixing to homogeneity, the other ingredients of Group 1 (see Table 2) were added. Mixing to homogeneity was repeated and then the temperature was increased to 85° C. to 90° C. At this temperature the ingredients of Group 2 (see Table 2) were added and mixed in until homogeneity was achieved. This was then repeated with the ingredients of Group 3 (3a and 3b, see Table 2). The ingredients of Group 4 (see Table 2) were homogeneously mixed together and also added to the previously prepared mixture and blended in until homogeneity was achieved. Afterwards, the temperature was no longer actively maintained at 85° C. to 90° C., but it was only ensured that it did not drop to 70° C. or less. Finally, the mixture was kept at a temperature above 70° C. for filling or packaging.

This was followed by the introduction of a gas selected from air, $N_2$, $N_2O$ and/or $CO_2$ at a pressure of 2 to 40 bar or alternatively the introduction of air with a high speed mixer, extrusion of the gassed mixture from a desired shaping port or into a desired mold and solidification/cooling of the extrudate in the desired shape and removal of the extrudate from the mould or cutting and portioning of the extrudate. The cosmetic compositions obtained had densities ranging from 0.2 g/cm³ to 1.2 g/cm³.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A solid cosmetic composition consisting of:
water in an amount of from 18 to 36.5% by weight;
citric acid in an amount of 0.25% by weight;
cetrimonium chloride in an amount of 8% by weight;
glycerol in an amount of 35% by weight;
cetearyl alcohol in an amount of from 2 to 5% by weight;
a combination of palmitic acid and stearic acid in an amount of from 2 to 5% by weight;
glyceryl stearate in an amount of 2.5 to 5% by weight;
maltodextrin in an amount of 1% by weight;
hydroxypropyl starch phosphate in an amount of 1.5% by weight;
*Zea mays* starch in an amount of from 10 to 17.25% by weight;
*Butyrospermum parkii* (shea) butter in an amount of 0.5% by weight;
apricot kernel oil in an amount of 2% by weight;
perfume in an amount of 0.5% by weight;
phenoxyethanol in an amount of 1% by weight; and
air, $N_2$, $N_2O$ and/or $CO_2$ incorporated thereinto form the solid composition,
wherein the composition is solid at about 25° C. and is a three-dimensional, dimensionally stable structure which is not a liquid or gas; and wherein the composition has a density of from 0.2 g/cm³ to 1.2 g/cm³.

2. The solid cosmetic composition according to claim 1 wherein
the water is present in an amount of 18% by weight;
the cetearyl alcohol is present in an amount of 5% by weight;
the combination of palmitic acid and stearic acid is present in an amount of 5% by weight;
the glyceryl stearate is present in an amount of 5% by weight; and
the *Zea mays* starch is present in an amount of 17.25% by weight.

3. The solid cosmetic composition according to claim 1 wherein
the water is present in an amount of 36.5% by weight;
the cetearyl alcohol is present in an amount of 2% by weight;
the combination of palmitic acid and stearic acid is present in an amount of 2% by weight;
the glyceryl stearate is present in an amount of 2.5% by weight; and
the *Zea mays* starch is present in an amount of 10% by weight.

4. A method for preparing a solid cosmetic composition according to claim 1, comprising:
a. adding all ingredients into a container to form a mixture,
b. heating the mixture until all ingredients are melted or uniformly dispersed,
c. introducing the air, $N_2$, $N_2O$ and/or $CO_2$ into the heated mixture at a pressure of from about 2 to about 40 bar, or by introducing air with a high speed mixer, making an aerated mixture;

d. extruding the aerated mixture from a desired shaping port, or into a desired mold,
e. solidifying the extrudate in the desired form, and
f. removing the extrudate from the mold or cutting and portioning the extrudate.

5. A method of using a solid cosmetic composition according to claim 1, comprising mixing the solid composition with water and then applying the composition mixed with water to hair.

6. A method of using a solid cosmetic composition according to claim 1, comprising applying the solid composition directly to wet hair.

7. A method of using a solid cosmetic composition according to claim 1 comprising moistening, impregnating or emulsifying the composition with water, distributing it on hair and after an exposure time of from about 5 seconds to about 5 minutes, optionally rinsing out again with water.

* * * * *